United States Patent [19]

Patel et al.

[11] Patent Number: 5,364,623
[45] Date of Patent: Nov. 15, 1994

[54] **ANTIBIOTIC PRODUCED BY *BACILLUS SUBTILIS* ATCC 55422 CAPABLE OF INHIBITING BACTERIA**

[75] Inventors: Pramathesh S. Patel, Ringoes, N.J.; Friedrich Mayerl, Norwalk, Conn.; Edward Meyers, East Brunswick, N.J.

[73] Assignee: Bristol-Myers Squibb Company, Princeton, N.J.

[21] Appl. No.: 55,162

[22] Filed: Apr. 30, 1993

[51] Int. Cl.[5] .................... A61K 35/00; C12P 1/00; C12P 7/00; C12P 1/04
[52] U.S. Cl. .................................. 424/116; 422/1; 435/41; 435/132; 435/170; 435/252.5; 435/839
[58] Field of Search ............... 424/116, 252.5; 435/252.5, 41, 132, 170, 839; 422/1

[56] References Cited

U.S. PATENT DOCUMENTS

| | | | |
|---|---|---|---|
| 3,721,684 | 3/1973 | Meyers et al. | 424/121 |
| 3,856,938 | 12/1974 | Murao et al. | 424/116 |
| 4,296,101 | 10/1981 | Weisenborn et al. | 424/119 |
| 4,548,816 | 10/1985 | Kondo et al. | 424/116 |
| 4,681,846 | 7/1987 | Wilson et al. | 435/124 |
| 5,008,191 | 4/1991 | Okazaki et al. | 435/124 |
| 5,061,495 | 10/1991 | Rossall | 435/252.5 |
| 5,070,015 | 12/1991 | Petuch et al. | 435/839 |
| 5,158,960 | 10/1992 | Meyers et al. | 514/314 |

FOREIGN PATENT DOCUMENTS 0722433 1/1955 United Kingdom ............... 435/839

OTHER PUBLICATIONS

Watanabe et al. (1982) The Journal of Antibiotics, 35(9), 1141–1147.
Zimmermann et al. (1987) The Journal of Antibiotics, 49(12), 1677–1681.
Wilson et al, (1987) The Journal of Antibiotics, 40(12), 1682–1691.
Zweerink et al. (1987) The Journal of Antibiotics, 40(12), 1692–1697.
Mulks et al. (1990) Antimicrobics Agents and Chemotherapy, 34(9), 1762–1765.
Watanabe et al. (1991) The Journal of Antibiotics, 44(12) 1457–1499.
Nakajima et al. (1987) Chem. Phar. Bull. 35(6), 2228–2237.
Mallams et al. (1983) J. Chem. Soc. Perkin Trans. I, 7, 1497–1534.
Pramarik et al. (1984) J. Antibiot., 37(71), 818–21.

*Primary Examiner*—Douglas W. Robinson
*Assistant Examiner*—Jeffrey J. Sevigny
*Attorney, Agent, or Firm*—Suzanne E. Babajko

[57] ABSTRACT

The invention is drawn to an antibiotic produced by *Bacillus subtilis* ATCC 55422 having a nominal molecular weight of 580 and the empirical formula $C_{35}H_{48}O_7$, or a salt thereof. The antibiotic is useful in inhibiting the growth of bacteria, including Escherichia, Klebsiella, Proteus, Serratia, Bacillus and Staphylococcus.

5 Claims, 4 Drawing Sheets

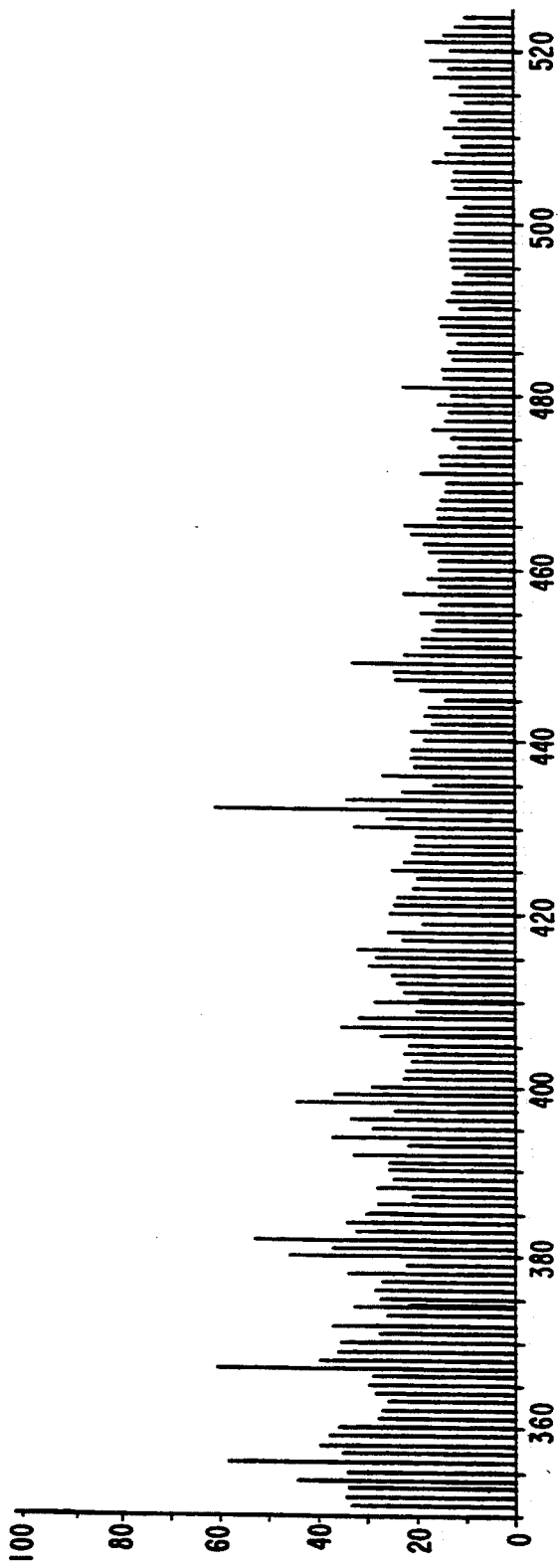
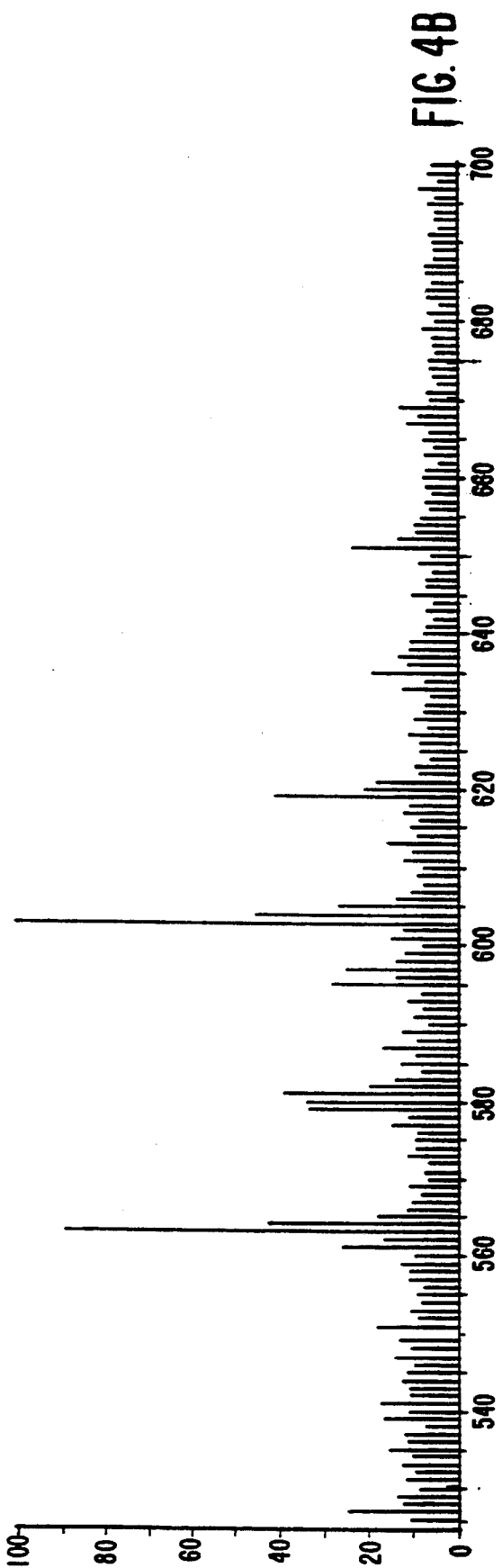

ANTIBIOTIC PRODUCED BY *BACILLUS SUBTILIS* ATCC 55422 CAPABLE OF INHIBITING BACTERIA

FIELD OF THE INVENTION

The present invention relates to the novel antibiotic bacillaene, which may be obtained by cultivation of a strain of Bacillus subtilis.

SUMMARY OF THE INVENTION

The present invention provides the novel compound bacillaene having antibacterial activity, and salts thereof. The present invention also provides a method for the preparation of bacillaene, comprising the step of cultivating the microorganism Bacillus subtilis A.T.C.C. 55422. The present invention further provides novel antibacterial compositions comprising bacillaene or salts thereof, and methods of using the inventive compounds as antibacterial agents.

BRIEF DESCRIPTION OF DRAWINGS

FIG. 4 shows the mass spectrum of bacillaene (FAB-mode).

DETAILED DESCRIPTION OF THE INVENTION

Figure 1:
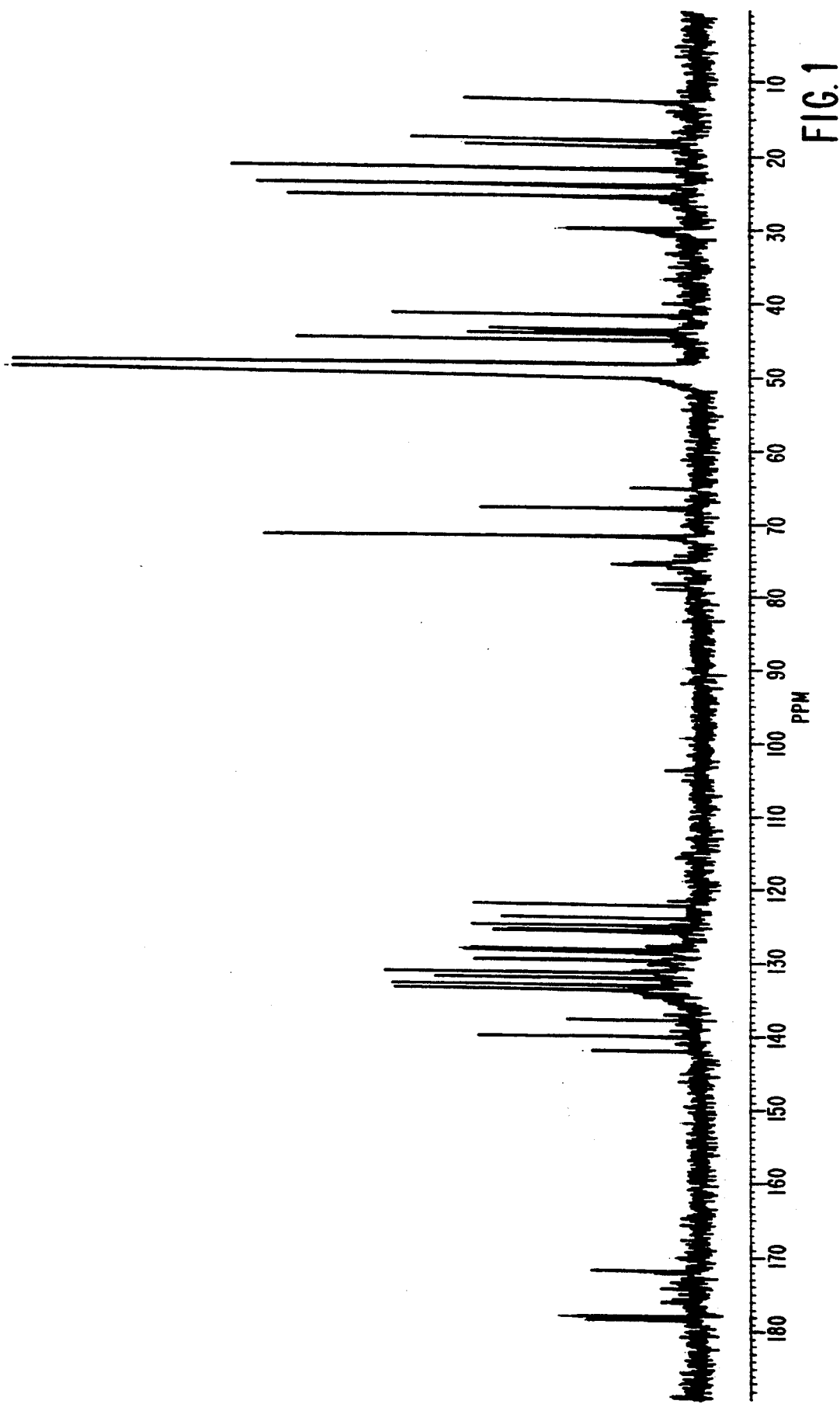
FIG. 1 shows the $^{13}C$ NMR spectrum of bacillaene in $CD_3OD$ (125 MHz, shifts in ppm).

The present invention is described further as follows.

The Microorganism

The microorganism which may be used for the production of bacillaene is a strain of *Bacillus subtilis* isolated from a soil sample obtained in Tokyo Shrine, Tokyo, Japan. A subculture of this strain can be obtained from the American Type Culture Collection, 12301 Parklawn Drive, Rockville, Md. 20852. Its accession number in this repository is A.T.C.C. 55422, deposited on Apr. 21, 1993. In addition to the specific microorganism described and characterized herein, it should be understood that a strain of *Bacillus subtilis* having the identifying characteristics of the strain designated by A.T.C.C. 55422 capable of producing bacillaene, or mutants of the specific microorganism described and characterized herein, such as those produced by the use of chemical or physical mutagens including X-rays, ultra-violet radiation, mutagens, etc., as well as genetic constructs of the microorganism, may also be cultivated to produce bacillaene.

*Bacillus subtilis* A.T.C.C. 55422 may be isolated from a soil sample in which it is present by first suspending the sample in a sterile diluent (e.g., buffered saline solution containing 0.01% gelatin) and shaking vigorously. A dilution of this suspension may be plated onto a nutrient medium that has been supplemented with cycloheximide. In accordance with the above, soil (in this case from a soil sample obtained from Tokyo Shrine, Tokyo, Japan) was prepared and plated as follows:

About 0.5 g soil sample was aseptically placed in a 1×6 tube (with Morton cap) containing 10 ml of sterile B-NaCl-G. (B-NaCl-G contains: NaCl (8.5 g), $KH_2PO_4$ (0.3 g), $Na_2HPO_4$ (0.6 g), gelatin (0.1 g), and distilled water (1 liter)). The mixture was vortexed, sonicated for 10 minutes using a Branson sonicator, and serially diluted with B-NaCl-G. The mixture was then spread at 0.1 ml dilution onto isolation plates containing isolation agar ("Ex Min+" described following) using a sterile glass rod. The plates were incubated at room temperature for 5 days. Subculture bacterial isolates were placed onto Medium H107 having the following composition:

| | |
|---|---|
| Soil extract | 200 ml |
| Tap water | 800 ml |
| Agar | 17.5 g |
| Yeast extract | 5.0 g |
| Glucose | 5.0 g |
| $MgSO_4.7H_2O$ | 0.1 g |
| $FeSO_4.7H_2O$ | 0.1 g |
| Sterilize at 121° C. for 15 minutes. | |

The isolation agar Ex Min+ contained the following:

| | |
|---|---|
| yeast extract | 2.5 g |
| peptone | 2.0 g |
| beef extract | 5.0 g |
| $MgSO_4.7H_2O$ | 0.5 g |
| $FeSO_4.7H_2O$ | 0.2 g |
| glucose | 2.0 g |
| NaCl | 0.1 g |
| agar | 20.0 g |
| distilled water | 1 liter |
| (final pH without adjustment: 6.6) | |

After autoclaving, the following filter-sterilized solutions were added to the isolation agar: 1% aqueous cycloheximide (10.0 ml/liter of agar); and 1.0 mg/ml aqueous colistin (10.0 ml/liter of agar).

Cultures of *Bacillus subtilis* A.T.C.C. 55422 which have been obtained as above exhibit the following characteristics:

(a) Morphological and Physiological Characteristics

Gram-positive rods; ellipsoidal spores central to terminal. Citrate is utilized; nitrate is reduced to nitrite; starch is hydrolyzed; gelatin is hydrolyzed, and acetylmethylcarbinol is produced.

(b) Fermentation Characteristics

Glucose, mannitol, xylose, arabinose and sucrose are utilized oxidatively; glucose and sucrose are fermented.

These characteristics are in agreement with those described for *Bacillus subtilis* by Ruth Gordon, Agricultural Handbook #427, Agricultural Research Services, USDA, Washington, D.C., and therefore establish the identity of the organism as *Bacillus subtilis*. Biologically pure *Bacillus subtilis* A.T.C.C. 55422 is novel.

Preparation of Bacillaene

Cultivation of the microorganism *Bacillus subtilis* A.T.C.C. 55422 yields the novel antibacterial substance bacillaene. Bacillaene may be formed as a metabolite thereof.

To prepare bacillaene, *Bacillus subtilis* A.T.C.C. 55422 may be cultivated (fermented), for example, at about 25° C. under submerged aerobic conditions in an aqueous nutrient medium containing assimilable carbon (carbohydrate) and nitrogen sources until antibiotic activity due to bacillaene is imparted to the medium. The fermentation may be carried out for a time period such as approximately 48 hours, at the end of which time the antibiotic bacillaene has been formed, and may be isolated from the fermentation medium and purified.

After the fermentation has been completed, the fermented broth may be filtered and the pH of the filtrate adjusted to about 6.5 by the addition of hydrochloric acid. The filtrate may then be extracted with a water immiscible organic solvent, for example, with ethyl acetate or n-butanol saturated with water (e.g. twice, such as with 0.3 volumes of n-butanol saturated with water per volume of broth each time). The combined organic layers (e.g. pooled butanol extracts) may be concentrated in vacuo (e.g. at $\leq 40°$ C.) to an oily residue ("syrup"). The oil may be mixed with a small amount of methanol and chromatographed on a column on CHP20P resin (Mitsubishi Chemical Industries, Ltd. Japan) prepared in a starting buffer consisting of 10 mM phosphate at pH 6.5. After introduction of the sample, a linear gradient from starting buffer to pure methanol may be applied, followed by elution with pure methanol. Active fractions elute towards the end of the gradient and may be further purified by reversed phase chromatography on C-18 silica gel using a linear gradient of methanol in water.

The Antibiotic and Use Thereof

Figure 2:
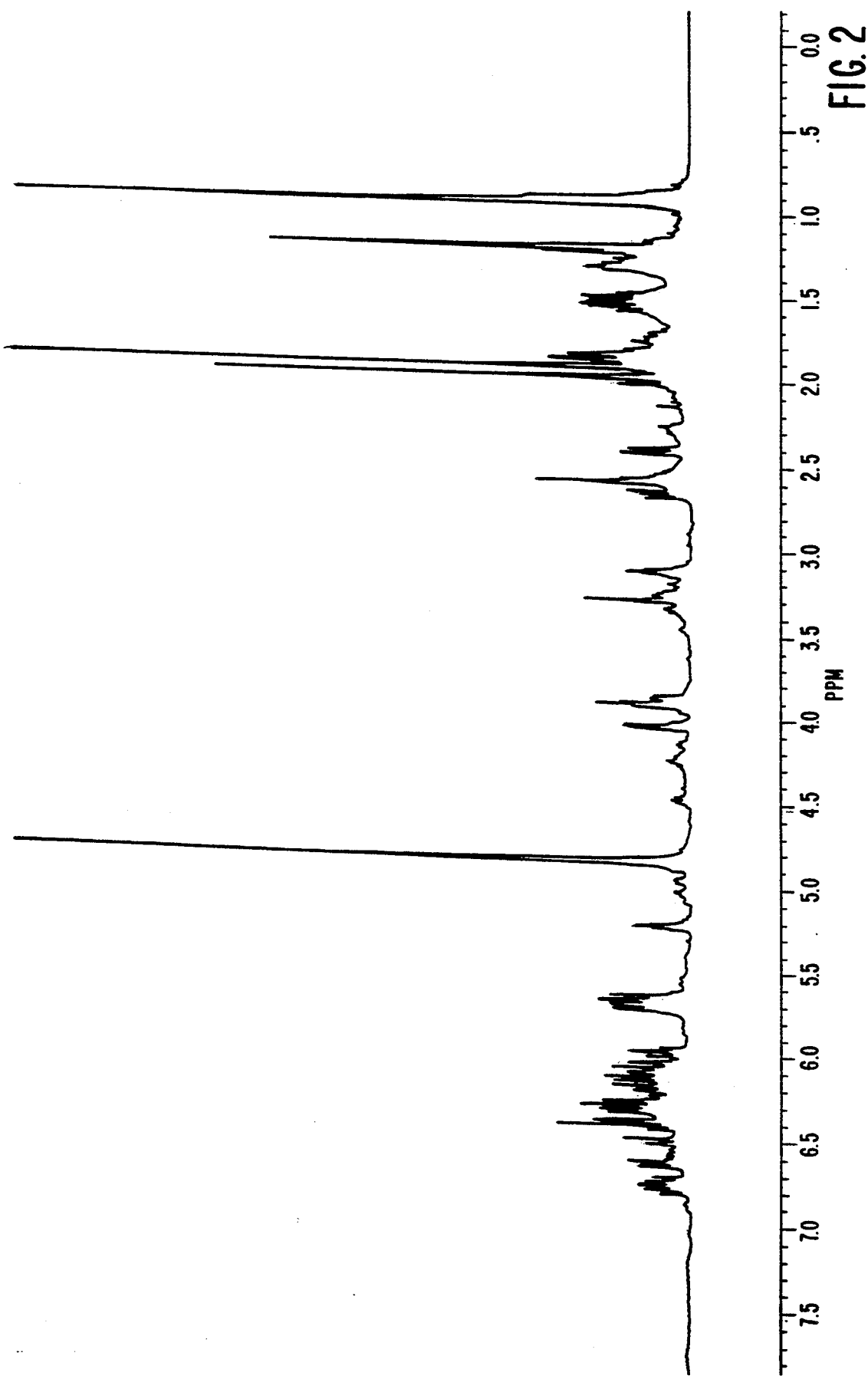
FIG. 2 shows the $^{1}H$ NMR spectrum of bacillaene in $CD_3OD$ (500 MHz, shifts in ppm).
Figure 3:
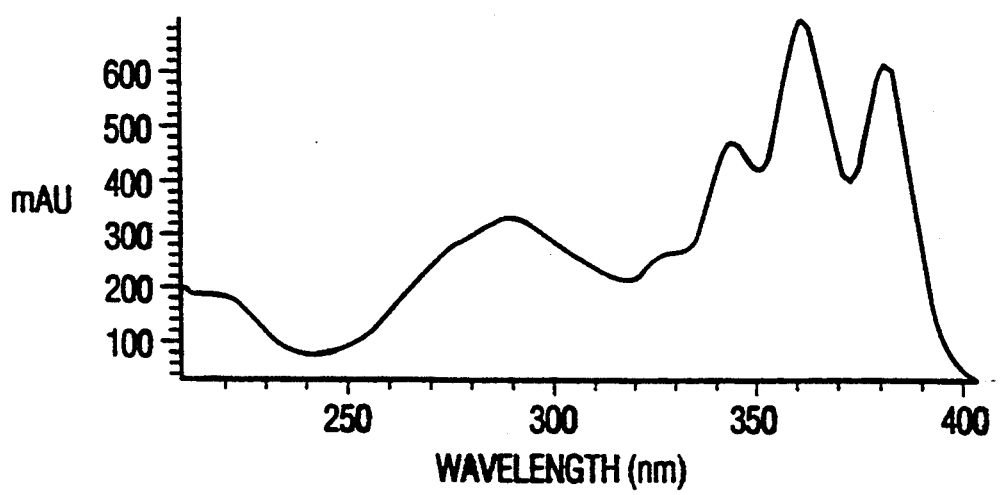
FIG. 3 shows the ultraviolet (UV) spectrum of bacillaene in methanol.

Bacillaene possesses antibacterial properties, and has been found to have the characteristics shown in the Figures and in Example 1 herein, especially:
the $^{13}$C NMR spectrum in CD$_3$OD (125 MHz, shifts in ppm) shown in FIG. 1;
the $^1$H NMR spectrum in CD$_3$OD (500 MHz, shifts in ppm) shown in FIG. 2;
the ultraviolet (UV) spectrum in methanol shown in FIG. 3; and
the mass spectrum (FAB-mode) shown in FIG. 4.

The compounds of the present invention include bacillaene and salts thereof. The term "salts", as used herein, denotes acidic and/or basic salts, formed with inorganic and/or organic acids and bases. While pharmaceutically acceptable salts are preferred, particularly when employing the compounds of the invention as medicaments, other salts find utility, for example, in processing these compounds, or where non-medicament-type uses are contemplated.

It is preferred that the inventive compounds have a degree of purity such that they are suitable for use as antibiotic agents. A particularly preferred embodiment of the instant invention provides bacillaene or a salt thereof in a substantially pure state. The substantially pure compounds are preferably employed in the compositions and methods described following.

The inventive compounds are useful as antimicrobial agents, useful in inhibiting the growth of microorganisms, particularly bacteria such as gram positive and gram negative bacteria, for example, bacteria of the genera Escherichia, Klebsiella, Proteus, Serratia, Bacillus and Staphylococcus. Inhibition of the growth of a bacterium may be achieved by contacting the bacterium with a compound of the present invention in an amount effective therefor. In vitro mode of action studies indicate that bacillaene is a potent inhibitor of procaryotic protein synthesis.

Thus, the compounds of the present invention may be employed in utilities suitable for antibacterial agents.

The inventive compounds may, for example, be used in treating a host infected with a bacterium, comprising the step of administering to the host bacillaene or a physiologically tolerated salt thereof in an amount effective for the treatment. Treatment of such infections according to the instant invention includes both mitigation as well as elimination thereof.

Hosts treatable according to the method of the present invention include plants and animals, particularly mammals such as dogs, cats and other domestic animals and, especially, humans. The dosage form and mode of administration, as well as the dosage amount, may be selected by the skilled artisan. The dosage amount will vary with the severity of the infection, and with the size and species of the host. Exemplary daily dosages for an adult human are those within the range of from about 2.5 mg to about 2,000 mg/day. Administration to a mammalian host, may, for example, be oral, parenteral, or topical. Administration to a plant host may be accomplished, for example, by application to seed, foliage or other plant part, or to the soil.

Compositions are also provided by the present invention which comprise bacillaene or a physiologically tolerated salt thereof in an amount effective for the treatment of infection by a microorganism, and a physiologically tolerated vehicle or diluent. The term "physiologically tolerated" is equivalent to the term "pharmaceutically acceptable" when used in reference to the treatment of a mammalian host. The appropriate solid or liquid vehicle or diluent may be selected, and the compositions prepared, by methods known to the skilled artisan. Treatment of simultaneous infections by more than one bacterium is, or course, contemplated.

The inventive compounds may also be employed as antibacterial agents useful in inhibiting the growth of microorganisms present on a surface or in a medium outside a living host. The present invention therefore provides a method for inhibiting the growth of at least one microorganism present on a surface or in a medium, comprising the step of contacting the surface or medium with bacillaene or a salt thereof in an amount effective for the inhibition. Thus, the inventive compounds may be employed, for example, as disinfectants for a variety of solid and liquid media susceptible to microbial growth. Suitable amounts of the inventive compounds may be determined by methods known to the skilled artisan. Compositions comprising bacillaene or a salt thereof in an amount effective for inhibiting the growth of at least one bacterium, and a vehicle or diluent, are also provided by the present invention.

The following examples are provided to further illustrate the invention, and are not intended to in any way limit the scope of the instant claims.

EXAMPLE 1

Preparation of Bacillaene

Yeast beef agar slants were seeded with *Bacillus subtilis* A.T.C.C. 55422, and incubated for 24 to 48 hours at 25° C. The slants were then used to inoculate 100 ml of medium contained in 500 ml Erlenmeyer flasks. The composition of the germination medium was:

| | |
|---|---|
| Toasted Nutrisory flour | 15 g |
| Soluble starch | 15 g |
| Glucose | 50 g |
| CoCl$_2$.6H$_2$O | 0.005 g |
| CaCO$_3$ | 10 g |
| Distilled water | 1 L |
| Sterilized at 121° C. for 30 minutes. | |

The medium was subsequently held in shake flasks for 48 hours, allowing fermentation to occur. The contents of the shake flasks were then pooled to give ten liters of fermentation broth. The pH was adjusted to 6.5 with hydrochloric acid where necessary. Whole broth extraction was carried out by adding 8 liters of ethyl acetate and stirring the mixture at room temperature for thirty minutes. Centrifugation was employed to recover cells, and the aqueous and ethyl acetate layers. The recovered cells and aqueous phase were combined and extracted in a second step with a fresh portion of 4 liters of ethyl acetate. Most bacillaene, ca. 70 to 80% of the total, was extracted in the first step, as evidenced by UV spectroscopy of concentrated extracts. Bioautography of the extracts revealed the presence of bacillaene at Rf=0.76 using silica gel plates (E. Merck, Darmstadt) and eluting with 40% methanol in chloroform.

The extracts were combined and concentrated in vacuo to yield an oily residue which was mixed with five milliliters of methanol for application on a CHP20P column (5×30 cm, Mitsubishi Chemical Industries, Ltd. Japan). The column was prepared in 10 mM phosphate buffer at pH 6.5,and after injection of the sample, a linear gradient was run employing one liter of starting buffer and one liter of methanol. At the end of the gradient, elution was continued with pure methanol. A low pressure pump was used to provide a solvent flow rate of 20 ml/min. Initially, three 500 ml volumes were collected, followed by collecting fractions of 20 ml. The 20 ml fractions were checked for the presence of bacillaene by UV-spectrophotometry. Bacillaene eluted in fractions 27 to 40, together with other components of the extract. Pure bacillaene was obtained from these fractions by preparative HPLC on C-18 reversed phase silica gel (3×50 cm, 10 μm spherical; YMC, Inc., Wilmington, N.C.). The column was equilibrated in 40% methanol in water prior to applying the sample. Elution was effected by a linear gradient from 40% methanol to 100% methanol over 60 minutes followed by pure methanol. The flow rate was 50 ml/min and the detection wavelength was 360 nm. Fractions of 24 ml were collected with the bacillaene eluting in fractions 103 to 107. Fraction 104 was concentrated to give 8 mg of pure bacillaene for spectroscopic characterization.

UV-spectrum (methanol): characteristic bands at 343, 361, 382 nm. Mass spectrum (FAB-mode): m/z 619 (M+K), m/z 603 (M+Na), m/z 581 (M+H), m/z 563 (M+H—$H_2O$). High resolution m/z 603.3332 (M+Na). Molecular formula: $C_{35}H_{48}O_7$. Carbon-13 NMR spectrum ($CD_3OD$, 125 MHz, shifts in ppm): 178.6, 178.1, 172.0, 142.1, 140.2, 137.8, 133.9, 133.3, 132.2, 131.52, 131.49, 129.7, 128.9, 128.7 (2 signals), 128.5, 126.1, 125.7, 125.1, 124.0, 122.3, 71.8 (2 signals), 67.9, 44.5, 54.2, 43.7, 41.9, 25.9, 24.3, 22.1, 22.0, 18.9, 18.2, 12.9. H-NMR spectrum ($CD_3OD$, 500 MHz, shifts in ppm): several multiplets from 5.9 to 6.9, 5.70 (m), 5.22 (m), 4.05 (m), 3.92 (m), 3.12 (m), 2.65 (dxd), 2.40 (dxd), several multiplets and singlets from 0.8 to 2.0.

EXAMPLE 2

Bacillaene as Antibiotic

The following experiments were conducted, demonstrating the antibiotic properties of bacillaene.

(1) Determination of the minimum concentration of bacillaene required for total inhibition of growth (MIC) was performed using liquid H108 medium containing Bacto-Tryptone (10g); Bacto-yeast extract (5 g); NaCl (5 g); and distilled water (1 liter). The assays were performed in 13×100 mm glass tubes in a final volume of 0.5 ml. Two fold dilutions of the compound were utilized. The cultures were incubated at 37° C. in a test-tube rack on a shaker. Presence of turbidity was used as an indicator of growth. The tubes were read after 6–7 hours of incubation. Results obtained from the experiments performed to determine the MIC of bacillaene are shown in Table 1. Bacillaene appears to be extremely potent against certain strains of Escherichia coli.

TABLE 1

MIC determination using liquid broth tube dilution assays

| Organism | Strain # | Bacillaene (μg/ml) |
|---|---|---|
| Escherichia coli | K-10 | 37.0 |
| Escherichia coli | SGB-888+ | 0.09 |
| Escherichia coli | SGB-10857+ | 5.0 |
| Escherichia coli | BAS-2006+ | 0.60 |
| Escherichia coli | impB+ | 0.50 |

Organism from the general culture collection of Bristol-Myers Squibb Co.

(2) Bacillaene was determined to be a potent inhibitor of the procaryotic protein synthesis system as determined by measuring the incorporation of $^{35}S$ into trichloroacetic-acid-precipitable polypeptides. A prokaryotic in vitro transcription-translation coupled system was used for these experiments (Promega Corporation, 2800, Woods Hollow Road, Madison, Wis.). Bacillaene failed to inhibit the eucaryotic in vitro protein translation system at the concentrations tested (Promega Corporation, 2800,Woods Hollow Road, Madison, Wis.), indicating that bacillaene is a specific antibacterial agent.

The results obtained for these in vitro protein synthesis studies are shown in Table 2.

TABLE 2

Results of in vitro protein synthesis in the presence of bacillaene

| Final Conc. [μg/ml] | Procaryotic in vitro transc.-transl. sys. | Rabbit reticulocyte in vitro trans. sys. |
|---|---|---|
| 1.5 | >95.0% | <7.0% |
| 0.75 | >88.0% | <7.0% |
| 6.0 | N.D.+ | <7.0% |

+ N.D. = not determined

Bacillaene was also not observed to affect the growth of eukaryotic cells, viz. Saccharomyces cervesiae.

(3) The effect of bacillaene on a wide spectrum of bacteria was determined using the agar diffusion method. The bacteria to be tested were grown in H108 broth overnight at 37° C. This culture was used to inoculate H108 agar using a standard pour plate method. A 1% inoculum of the overnight culture was used. Wells of 2 mm diameter were punched in the agar and bacillaene (25 μg) was loaded in each well. The plates were incubated overnight at 37° C. and lack of growth around the agar well was scored as inhibition by bacillaene of the growth of the organism. The results obtained are shown in Table 3.

TABLE 3

| Culture | Strain Number* | Growth Inhibition |
|---|---|---|
| Escherichia coli | SC-10909 | +++ |

TABLE 3-continued

| Culture | Strain Number* | Growth Inhibition |
|---|---|---|
| Klebsiella pneumoniae | SC-10440 | + |
| Klebsiella pneumoniae | SC-9527 | + |
| Proteus vulgaris | SC-9416 | ++++ |
| Proteus mirabilis | SC-3855 | +++ |
| Serratia marcescens | SC-9783 | ++++ |
| Bacillus thuringiensis | | +++ |
| Staphylococcus aureus | SC-2400 | ++ (hazy) |
| Staphylococcus aureus | 209P | ++ (hazy) |
| Staphylococcus epidermidis | SC-9087 | − |
| Pseudomonas aeruginosa | SC-9087 | − |

(+) = growth inhibition (multiple "+" signs indicate larger zones of inhibition);
(−) = no zone of inhibition observed at the concentration tested.
* = Organism from the general culture collection of Bristol-Myers Squibb Co.

What is claimed is:

1. The compound bacillaene having the $^{13}$C NMR spectrum in CD$_3$OD (125 MHz, shifts in ppm) shown in FIG. 1; the $^1$NMR spectrum in CD$_3$OD (500 MHz, shifts in ppm) shown in FIG. 2; the ultraviolet (UV) spectrum in methanol shown in FIG. 3; the mass spectrum (FAB-mode) shown in FIG. 4; a nominal molecular weight of 580 and the empirical formula $C_{35}H_{48}O_7$, or a salt thereof.

2. The compound of claim 1 which is bacillaene.

3. A method for inhibiting the growth of a bacterium comprising the step of contacting said bacterium with an inhibiting amount of a compound of claim 1.

4. A composition for the inhibition of the growth of a bacterium comprising a compound of claim 1 in an amount effective for said inhibition and a vehicle or diluent.

5. A compound of claim 1 which is substantially pure.

* * * * *

UNITED STATES PATENT AND TRADEMARK OFFICE
CERTIFICATE OF CORRECTION

PATENT NO. : 5,364,623

DATED : November 15, 1994

INVENTOR(S) : Pramathesh S. Patel et al.

It is certified that error appears in the above-identified patent and that said Letters Patent is hereby corrected as shown below:

Column 8;
Claim 1, line 3, "$^1$NMR" should read --$^1$H NMR--.

Signed and Sealed this

Seventeenth Day of January, 1995

Attest:

BRUCE LEHMAN

Attesting Officer     Commissioner of Patents and Trademarks